(12) United States Patent
Hyun

(10) Patent No.: US 6,551,279 B1
(45) Date of Patent: Apr. 22, 2003

(54) INFUSION DISPENSER WITH ADJUSTABLE FLOW RATE REGULATOR

(75) Inventor: Dongchul D. Hyun, Brea, CA (US)

(73) Assignee: Oratec Interventions, Inc., Menlo Park, CA (US)

( * ) Notice: Subject to any disclaimer, the term of this patent is extended or adjusted under 35 U.S.C. 154(b) by 0 days.

(21) Appl. No.: 09/578,988

(22) Filed: May 25, 2000

(51) Int. Cl.$^7$ ............................................ A61M 37/00
(52) U.S. Cl. ...................................................... 604/132
(58) Field of Search ................................ 604/132, 133, 604/134, 135, 136, 137, 138, 142, 72, 80, 81, 93.01, 131

(56) References Cited

U.S. PATENT DOCUMENTS

| | | |
|---|---|---|
| 788,176 A | 4/1905 | Traves |
| 926,197 A | 6/1909 | Kim |
| 2,023,026 A | 12/1935 | Miller |
| 2,471,623 A | 5/1949 | Hubbell |
| 2,907,325 A | 10/1959 | Burke |
| 3,003,500 A | 10/1961 | Barton et al. |
| 3,054,401 A | 8/1962 | Gewecke |
| RE26,006 E | 4/1966 | Gewecke |
| 3,910,442 A * | 10/1975 | Gargano ..................... 215/218 |
| 4,038,983 A | 8/1977 | Mittleman et al. |
| 4,303,175 A * | 12/1981 | Lux ............................. 220/281 |
| 4,363,321 A * | 12/1982 | Chittenden .................. 604/131 |
| 4,397,642 A * | 8/1983 | Lamadrid ............. 128/DIG. 13 |
| 4,572,410 A * | 2/1986 | Brunet ..................... 222/402.1 |
| 4,735,613 A | 4/1988 | Bellin et al. |
| 4,909,786 A * | 3/1990 | Gijselhart et al. ... 128/DIG. 13 |
| 4,953,753 A | 9/1990 | Gortz |
| 5,005,604 A | 4/1991 | Aslanian |
| 5,135,500 A | 8/1992 | Zbed |
| 5,139,201 A * | 8/1992 | De Laforcade .......... 222/402.1 |
| 5,281,202 A | 1/1994 | Weber et al. |
| 5,330,431 A | 7/1994 | Herskowitz |
| 5,336,190 A | 8/1994 | Moss et al. |
| 5,529,214 A | 6/1996 | Lasonde et al. |
| 5,810,778 A * | 9/1998 | Hjertman ..................... 604/143 |
| 5,885,532 A * | 3/1999 | Maltabes et al. ........... 422/100 |
| 5,891,096 A | 4/1999 | Hyun et al. |
| 6,193,689 B1 * | 2/2001 | Woodard ..................... 604/122 |

FOREIGN PATENT DOCUMENTS

WO WO 95/00194 * 1/1995 ............ A61M/5/75

OTHER PUBLICATIONS

Novacon Corporation; "Rate Adjustable Ranger Infusion Device"; 4 pages.

* cited by examiner

*Primary Examiner*—Teresa Walberg
*Assistant Examiner*—Daniel Robinson
(74) *Attorney, Agent, or Firm*—Fish & Richardson P.C.

(57) ABSTRACT

A liquid medicament dispenser for controlled infusion delivery of liquid medication to a patient. The dispenser includes an elastomeric bladder for housing the liquid medication, an inlet in communication with the bladder for receiving the liquid medication into the bladder, and an outlet in communication with the bladder for discharging the liquid medication into an infusion tube for delivering the liquid medication to the patient. A flow regulator for controlling flow rate of the liquid medication through the infusion tube includes a flow rate adjuster with a manually operable adjuster knob for setting flow rate and an encasement housing releasably securable about the adjuster knob for impeding access to the adjuster once the proper rate has been set. By so protecting the flow rate adjuster knob with the encasement housing, accidental or deliberate re-adjustment of flow rate, as may be caused by the patient, is minimized while advantageously providing medicinal treatment utility among most patients because of integral adjustability of flow rate control.

6 Claims, 1 Drawing Sheet

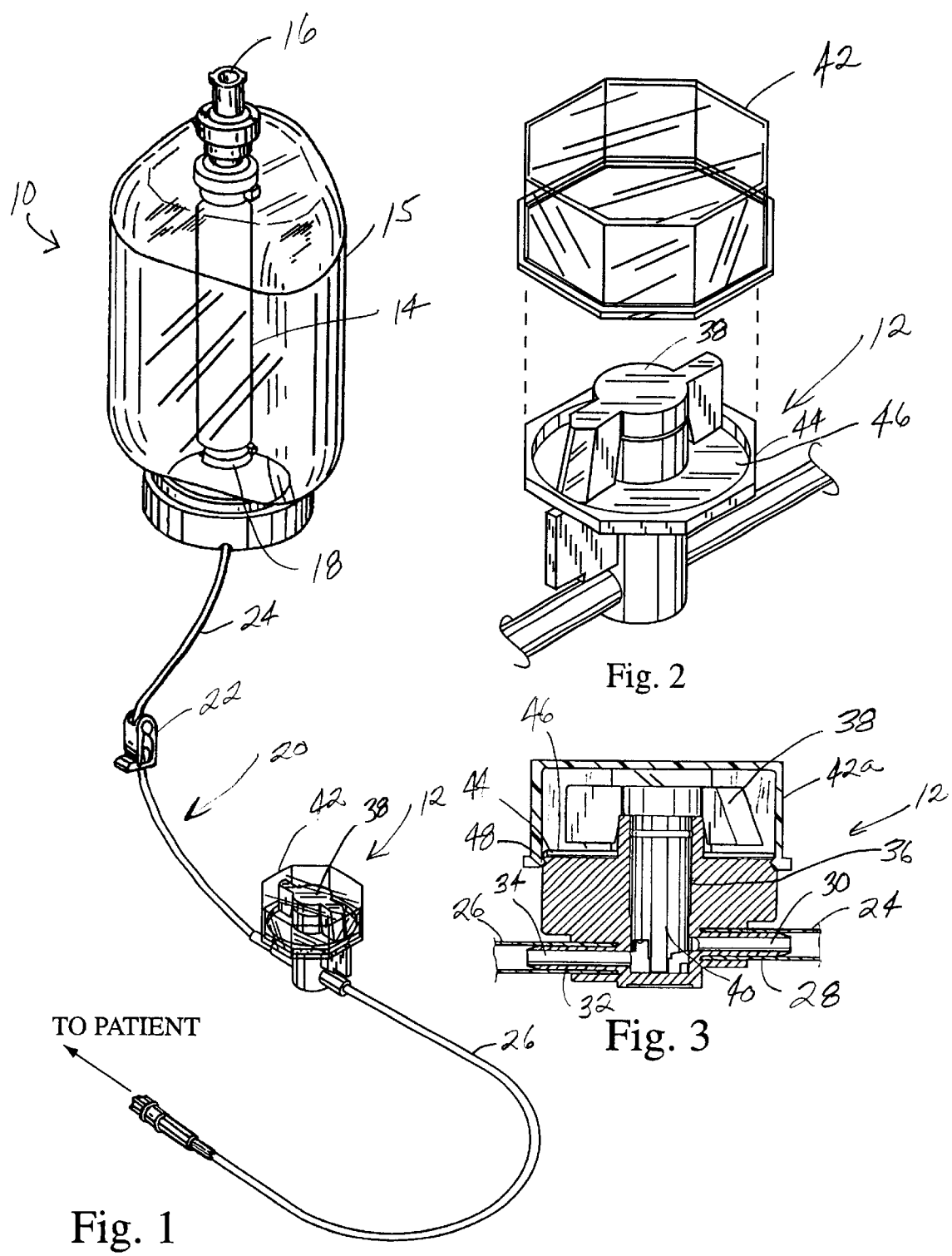

INFUSION DISPENSER WITH ADJUSTABLE FLOW RATE REGULATOR

BACKGROUND OF THE INVENTION

This invention relates in general to medication dispensers, and in particular to a liquid medicament dispenser for controlled infusion delivery of liquid medication to a patient wherein the dispenser is provided with a flow regulator for controlling flow rate of the liquid medication, a manually operable flow rate adjuster for setting flow rate, and an encasement housing releasably securable about the flow rate adjuster for impeding access to the adjuster once a flow rate has been set.

Many non-hospitalized and ambulatory patients regularly require an infusion delivery of intravenous (IV) liquid medication in a manner similar to that experienced by non-ambulatory hospitalized patients who are receiving a traditional IV drip from a hanging bottle. To address the need for such patients, manufacturers have developed portable infusion devices that can accompany the patient and accomplish controlled medication delivery while the patient attends to daily activities.

Most important in such drug delivery, however, is the provision of precise flow rates into the patient so that over- or under-medication does not occur. Because of this requirement, current portable infusion devices generally must be custom made with respect to flow rate values since these devices have no provision for flow rate adjustment. Consequently, manufacturers, wholesalers, and selling suppliers all must commit to extensive inventories of duplicate devices that differ individually only in flow rate delivery of infused medicaments.

In view of this flow-rate inflexibility in present infusion delivery devices, it is apparent that a need is present for flow rate adjustability. Consequently, a primary object of the present invention is to provide a controlled infusion delivery dispenser that includes a flow regulator with an easily adjustable flow rate.

Another object of the present invention is to provide a delivery dispenser having a flow rate adjuster with an encasement housing releasably securable there about for impeding access to the adjuster once a correct flow rate has been set.

These and other objects of the present invention will become apparent throughout the description thereof which now follows.

BRIEF SUMMARY OF THE INVENTION

The present invention is a liquid medicament dispenser for controlled infusion delivery of liquid medication to a patient. The dispenser includes an elastomeric bladder for housing the liquid medication under pressure imposed by the bladder, an inlet in communication with the bladder for receiving the liquid medication into the bladder, and an outlet in communication with the bladder for discharging the liquid medication from the bladder into an infusion tube leading from the outlet for delivering the liquid medication to the patient. A flow regulator for controlling flow rate of the liquid medication through the infusion tube, and which can be inline with the infusion tube, includes a flow rate adjuster with a manually operable adjuster knob for setting flow rate and an encasement housing releasably securable about the adjuster knob for impeding access to the adjuster once the proper rate has been set. By so protecting the flow rate adjuster knob with the encasement housing, accidental or deliberate re-adjustment of flow rate, as may be caused by the patient, is minimized while advantageously providing a medicament dispenser having utility among most all patients because of integral adjustability of flow rate control.

BRIEF DESCRIPTION OF THE SEVERAL VIEWS OF THE DRAWINGS

An illustrative and presently preferred embodiment of the invention is shown in the accompanying drawings in which:

FIG. 1 is a perspective view of a liquid medicament dispenser for controlled infusion delivery of liquid medication to a patient;

FIG. 2 is an exploded perspective view of the flow regulator of the dispenser of FIG. 1; and FIG. 3 is a side elevation view in section of the flow regulator of FIG. 2.

DETAILED DESCRIPTION OF THE INVENTION

Referring to FIGS. 1–3, a liquid medicament dispenser 10 having a flow regulator 12 for controlling flow rate of liquid medication is illustrated. The dispenser 10, except for the flow regulator 12, is substantially identical to the infusion pump shown and described in U.S. Pat. No. 5,529,214, issued Jun. 25, 1996, and incorporated herein by reference in its entirety. Additionally, the flow regulator 12 is substantially identical to the flow regulator shown and described in International Patent Application No. PCT/EP94/01908, corresponding to International Publication No. WO 95/00194, published Jan. 5, 1995, and incorporated herein by reference in its entirety. Thus, an elastomeric bladder 14 houses liquid medication introduced thereto as with a syringe or similar device through an inlet 16 in communication with the bladder 14, and maintains the medication under pressure as induced by the elastomeric property of the bladder 14. A protective housing 15 preferably surrounds the bladder 14. An outlet 18 in communication with the ladder 14 allows discharge of the medication into an infusion tube leading from the outlet 18 to a patient. A conventional squeeze clamp 22 is provided to the tube 20 for selectively closing or opening the tube 20.

In the embodiment here shown, the infusion tube 20 is separated into a first section 24 and a second section 26, with the flow regulator 12 disposed there between. In particular, the distal end 28 of the first section 24 of the tube 20 encompasses an upstream intake duct 30 of the regulator 12, while the proximal end 32 of the second section 26 encompasses a downstream discharge duct 34 of the regulator 12. A valve part formed as a cylindrically-shaped rotatable flow rate adjuster 36 terminates upwardly as a manually operable adjuster knob 38 for hand operation when setting flow rate. By rotating the adjuster knob 38, the configured cylinder 40 of the flow rate adjuster 36 controls the amount of liquid passing from the intake duct 30 to the discharge duct 34 by providing a variable opening whose variation is determined by amount of rotation of the adjuster 36 as accomplished by rotating the adjuster knob 38 thereof.

Surrounding the adjuster knob 38 is a releasably secured encasement housing 42 (FIGS. 1 and 2), 42a (FIG. 3) which can be non-opaque as shown in FIGS. 1 and 2, or opaque as shown in FIG. 3, and preferably fabricated of plastic. The housing 42, 42a engages the perimeter 44 of a top cover 46 of the flow regulator 12 by friction fit and by a perimeter lip 48 that resides beneath the perimeter 44 of the top cover 46, thereby intentionally making its removal difficult and impeding access to the adjuster knob 38. Fabricating the housing 42a of an opaque material can further reduce potential access to the adjuster knob 38 since a patient may not even realize that the thus non-viewable adjuster knob 38 exists.

Operability of the dispenser 10 is initiated by a health care professional who sets the flow rate of the flow regulator 12 by rotating the adjuster knob 38 to arrive at a flow rate that is therapeutically correct for a particular patient. Because of variations in viscosity and pressure delivery among liquids, a proper flow rate generally must be established through trial and error in accord with medical needs. Once the rate is determined as reflected in the setting of the adjuster 36, the encasement housing 42, 42a is securely positioned about the adjuster knob 38 as described above and the dispenser 10 is placed with the patient who typically self-administers the infused medication. As earlier noted, the encasement housing 42, 42a impedes access to the adjuster knob 38, either accidentally or intentionally, and thereby helps to assure maintenance of proper medication quantities for ambulatory patients.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A liquid medicament dispenser for controlled infusion delivery of liquid medication to a patient, the dispenser comprising:

a) an elastomeric bladder for housing the liquid medication under pressure imposed by said bladder;

b) an inlet in communication with the bladder for receiving the liquid medication into the bladder;

c) an outlet in communication with the bladder for discharging the liquid medication from the bladder;

d) an infusion tube leading from the outlet for delivering the liquid medication to the patient; and e) a flow regulator for controlling flow rate of the liquid medication through the infusion tube, said regulator having a flow rate adjuster with a manually operable adjuster knob for setting flow rate, said regulator further including a perimeter and an encasement housing including a lip configured to releasably reside beneath the perimeter, wherein the encasement housing is releasably securable about the adjuster knob for impeding access to said adjuster knob.

2. A liquid medicament dispenser as claimed in claim 1 wherein the flow regulator is disposed inline in the infusion tube.

3. A liquid medicament dispenser as claimed in claim 2 wherein the infusion tube is separated into a first section and a second section and the flow rate regulator is disposed between said first and second sections, whereby the first section of the infusion tube leading from the outlet terminates in upstream communication with a valve providing a variable opening controllable by the flow rate adjuster and the second section of the infusion tube originates in downstream communication with said valve.

4. A liquid medicament dispenser as claimed in claim 1 additionally comprising a protective housing surrounding the elastomeric bladder.

5. A liquid medicament dispenser as claimed in claim 1 wherein the encasement housing is non-opaque.

6. A liquid medicament dispenser as claimed in claim 1 wherein the encasement housing is opaque.

* * * * *

UNITED STATES PATENT AND TRADEMARK OFFICE
CERTIFICATE OF CORRECTION

PATENT NO. : 6,551,279 B1
DATED : April 22, 2003
INVENTOR(S) : Dongchul D. Hyun

It is certified that error appears in the above-identified patent and that said Letters Patent is hereby corrected as shown below:

<u>Title page,</u>
Item [56], References Cited, U.S. PATENT DOCUMENTS, after "4,953,753", change "9/1990" to -- 8/1990 --.

<u>Column 2,</u>
Line 40, change "ladder 14" to -- bladder 14 --.
Line 41, change "infusion tube leading" to -- infusion tube 20 leading --.

Signed and Sealed this

Twentieth Day of January, 2004

JON W. DUDAS
*Acting Director of the United States Patent and Trademark Office*